(12) United States Patent
Teixeira Rangel

(10) Patent No.: US 12,150,500 B2
(45) Date of Patent: *Nov. 26, 2024

(54) CONFIGURATION IN PRODUCT MADE WITH RUBBER LIQUID SILICONE (LSR) INTENDED FOR COMFORT, PROTECTION, REHABILITATION AND BODY CARE

(71) Applicant: Ana Maria Teixeira Rangel, Norcross, GA (US)

(72) Inventor: Ana Maria Teixeira Rangel, Norcross, GA (US)

( * ) Notice: Subject to any disclaimer, the term of this patent is extended or adjusted under 35 U.S.C. 154(b) by 640 days.

This patent is subject to a terminal disclaimer.

(21) Appl. No.: 17/428,399

(22) PCT Filed: Apr. 7, 2021

(86) PCT No.: PCT/BR2021/050141
§ 371 (c)(1),
(2) Date: Aug. 4, 2021

(87) PCT Pub. No.: WO2022/213162
PCT Pub. Date: Oct. 13, 2022

(65) Prior Publication Data
US 2023/0354928 A1   Nov. 9, 2023

(30) Foreign Application Priority Data
Apr. 6, 2021   (BR) ...................... 20 2021 006557 0

(51) Int. Cl.
| | | |
|---|---|---|
| *A41D 13/015* | (2006.01) |
| *A41D 13/05* | (2006.01) |
| *A61F 7/02* | (2006.01) |
| *A61H 39/04* | (2006.01) |

(52) U.S. Cl.
CPC ................ *A41D 13/05* (2013.01); *A61F 7/02* (2013.01); *A61H 39/04* (2013.01); *A61F 2007/0219* (2013.01); *A61F 2007/0233* (2013.01)

(58) Field of Classification Search
CPC .............. A41D 13/015; A41D 19/0062; A61F 2007/0225; A61F 2007/0233; A61F 2007/0219
USPC ........................................................ 2/16, 24
See application file for complete search history.

(56) References Cited

U.S. PATENT DOCUMENTS

| | | | | |
|---|---|---|---|---|
| 909,215 | A | * | 1/1909 | Prince et al. ...... A63B 71/1225 |
| 942,003 | A | * | 11/1909 | Marsh .................... A61F 13/105 |
| 2,640,989 | A | * | 6/1953 | James ................ A41D 13/0568 2/22 |

(Continued)

FOREIGN PATENT DOCUMENTS

WO    WO-2013126727 A1 *  8/2013  ............. A41D 19/00

*Primary Examiner* — Tajash D Patel
(74) *Attorney, Agent, or Firm* — Johnson | Dalal; Mark C. Johnson

(57) ABSTRACT

"CONFIGURATION IN PRODUCT MADE WITH RUBBER LIQUID SILICONE (LSR) INTENDED FOR COMFORT, PROTECTION, REHABILITATION AND BODY CARE" deals with an unprecedented object produced in silicone to be used in the field of clothing and personal care accessories/trimmings, more precisely to elements to cover, protect, treat and rehabilitate the user's body parts during activities daily or rest, in different weather conditions and environments, as well as during sporting events, games, training or physical activities in general.

3 Claims, 6 Drawing Sheets

(56) References Cited

U.S. PATENT DOCUMENTS

| | | | | |
|---|---|---|---|---|
| 3,602,917 A * | 9/1971 | Seunevel | A41D 19/0062 | 2/167 |
| 5,031,240 A * | 7/1991 | Nierhaus | A41D 13/065 | 2/24 |
| 5,269,322 A * | 12/1993 | Mandel | A61F 5/3715 | 128/845 |
| 5,323,490 A * | 6/1994 | Yarbrough | A41D 19/0062 | 2/163 |
| 5,592,953 A * | 1/1997 | Delao | A61F 15/004 | 128/882 |
| 5,594,954 A * | 1/1997 | Huang | A41D 13/065 | 2/24 |
| 6,532,963 B2 * | 3/2003 | Swanbeck | A41D 13/087 | 128/880 |
| 6,807,682 B1 * | 10/2004 | Shircliff | A41D 13/0568 | 2/24 |
| 6,839,905 B1 * | 1/2005 | Bruder | A41D 13/087 | 2/21 |
| 9,801,422 B2 * | 10/2017 | Anstey | A41D 19/015 | |
| 11,224,525 B2 * | 1/2022 | Radspieler | A61F 2/7812 | |
| 11,412,788 B2 * | 8/2022 | Teixeira Rangel | A41D 13/015 | |
| 2007/0148409 A1 * | 6/2007 | Rios | B25G 1/10 | 428/167 |
| 2009/0035524 A1 * | 2/2009 | Wyner | B29C 66/436 | 428/156 |
| 2014/0163326 A1 * | 6/2014 | Forsell | A61B 17/3423 | 600/207 |
| 2016/0113834 A1 * | 4/2016 | Bring | A61H 7/007 | 601/134 |
| 2016/0303462 A1 * | 10/2016 | Ramirez | A63B 71/141 | |
| 2019/0387821 A1 * | 12/2019 | Eugene | A41D 19/01558 | |
| 2020/0100927 A1 * | 4/2020 | Eugene | A61F 5/019 | |
| 2024/0065352 A1 * | 2/2024 | Anstey | A41D 19/015 | |

\* cited by examiner

CONFIGURATION IN PRODUCT MADE WITH RUBBER LIQUID SILICONE (LSR) INTENDED FOR COMFORT, PROTECTION, REHABILITATION AND BODY CARE

This model deals with an unprecedented produced object in silicone to be used in the field of clothing and personal care accessories/trimmings, more precisely to elements to cover, protect, treat and rehabilitate the user's body parts during activities daily or rest, in different weather conditions and environments, as well as during sporting events, games, training or physical activities in general.

FUNDAMENTALS OF THE TECHNIQUE

In recent years, manufacturers clothing and protective equipment, and production sought to provide varying levels of comfort, protection and functionality together with specific types of protective accessories, using different materials, knitting/sewing and other techniques in an attempt to do not harm the skin.

STATE OF THE TECHNIQUE

In the current state of the art they can be found several products related to the silicone material that comes in contact with the skin.

In consultation with the Brazilian INPI database and the international databases, prove to be the most varied documents with said material, of which we will exemplify some more relevant ones, as follows.

PI 0907680-8, under the title: "Article", which reveals a invention related to articles comprising garments with at least one opening layer included. the articles may include an elastic polymer composition, such as a film, a molten material or an aqueous dispersion.

EP3121321A1, under the heading "Sleeve and device with graduated compression for the treatment and/or prevention of lymphodemas which refers to a therapeutic sleeve made of mesh fabric with graduated compression with features multifunctional and that favors conditions to prevent the appearance or worsening of lymphoedema in the limbs, preventing swelling in the limbs and increasing comfort thermophysiological, ergonomic and psychological of the user during use.

EP2549967B1, under the title "CLOTHING PIECE, IN PARTICULATE A COMPRESSION PIECE FOR MEDICINAL USE" that defines a garment (10; 100) including a portion of knitted welt extending circumferentially, having an anti-slip zone (50) comprising a high wire friction contact the user's skin to increase the anti-slip properties of the garment. the invention it also refers to a method for making such a garment.

WO2015117195A1, under the heading "Coated textile sock and anti-bubbles" formed by an elastic or knitted fabric (20) having an intertwining or integration of fibers, the textile having a first (12) and second surface opposites that correspond to an inner surface of the sock. (32) and an outer surface of the sock (34), respectively, the textile including silicone (22) applied to the first surface (12) and the silicone (22) being cured, the silicone (22) being applied and cured in such a way that the fibers of the textiles (20) are at least partially coated and the textile is porous.

The processes mentioned do not reveal properties related to skin health product and not even in settings that can be used in multiple parts of the body with comfort and safety, nor products like means of protection and relief from pain or injury. There is documents that reveal compression products for relief of pain, however, in them the silicone product has the simple function to make the socks not move.

PROPOSAL OF THE UTILITY MODEL

The present model aims to provide devices in the line of accessory/trimming, protective products, specifically to offer comfort, protection, safety for therapeutic and beauty treatments. Can be used on different parts of the body, with perfect adhesion, with high flexibility and elasticity adapting to different limb sizes and body shapes, respecting the differences of each individual and their movements, without displacement of the object. The objects are presented in configurations applied to gloves, socks, insoles, sleeves, hot and cold compresses, knee pads, elbow pads, among other objects, being made with a specific Silicone Rubber Liquid (LSR). This specific silicone, in addition to being recognized as a hypoallergenic material, it is also antifungal.

For the objects to be produced, silicone is injected into molds, which when solidified transforms on specific objects and on some of these objects a gel is inserted in strategic parts. Said gel can be cooled or heated, where the object is used as compress for pain relief and muscle rehabilitation.

The products that already exist, mentioned in the state of technique, has strong mention of compression, not attending to its users on the issue of flexibility in the joints of parts of the body where they are used, such as the knees, elbows, fingers etc, where limbs need be bent and when there is a compression of the place, this action it is uncomfortable, painful and uncomfortable.

What brings to light one of the main advantages of objects proposed in this model since the use of these inserted in parts of the body, provide comfort and mobility/convenience in use, since the portion pleated/pleated expands, varying the size in order to suit different users. The object also has a new concept of fully made sleeve (sleeve) with liquid silicone rubber which offers a total adhesion to the skin, avoiding displacement with the introduction innovative pleating/ruffle that enables bending the joints where applied (mobility); innovations that were not found in similar objects.

Another advantage is that the object can be heated or cooled down before use, since some of the objects receive the gel sheltered between the walls of the cured silicone thus offering analgesic care in the treatment of muscle pain and rehabilitation.

Another advantage of the objects introduced here as new, because they are made with rubber Liquid Silicone, offer a special protection between the apparatus worn by the user and the skin. It is known that the friction/friction between devices used by users (such as in sports, wearing social shoes and sports, etc.) when in contact with the skin, they provoke irritation, blisters and injuries to users' skin causing pain, limiting and even preventing users from perform your assignments. However, one of the properties of Liquid Silicone Rubber is its adhesion to the skin, therefore, innovative objects are made with liquid silicone rubber, form a protective layer acting as a second skin fully adherent to the user avoiding friction caused by direct skin contact with the apparatuses. This prevents the consequences caused by friction, such as: blisters, corns and other injuries, offering comfort and protection, and providing users perform better in their physical activities.

We can combine the advantages, applying them to objects specifics: hot/cold compresses allied to pleats/ruffles in knee and elbow pads; pleats/pleats combined with smooth silicones or with massage points, inserted in products that work like gloves and socks; reinforcements combined with ruffles/ruffles and perforations for skin breathing, preventing accumulation of sweat, in gloves and socks; smooth silicone with portions pleats/ruffles in strategic parts of the body (by example: joints for mobility and adaptation to the size of the user. In other words, the new applications achieved may be made available in objects with various characteristics, together or separately.

The products already existing and presented in the state of technique require immobility on the part of the user during the use. However, the objects shown here as new allow, during use, the full mobility of the user. This is because, in addition to the Liquid Silicone Rubber being pliable and elastic, the addition of ruffle/ruffle in the object allows flexion of the joint and also adaptation to the user size, thus allowing the user to make use of the limb (arm, leg, etc.) without being restricted to movements.

DESCRIPTION OF THE FIGURES

For a better and adequate understanding of the utility model, it becomes described below with the help of the attached figures, in which we will describe each of them.

Figure 1:
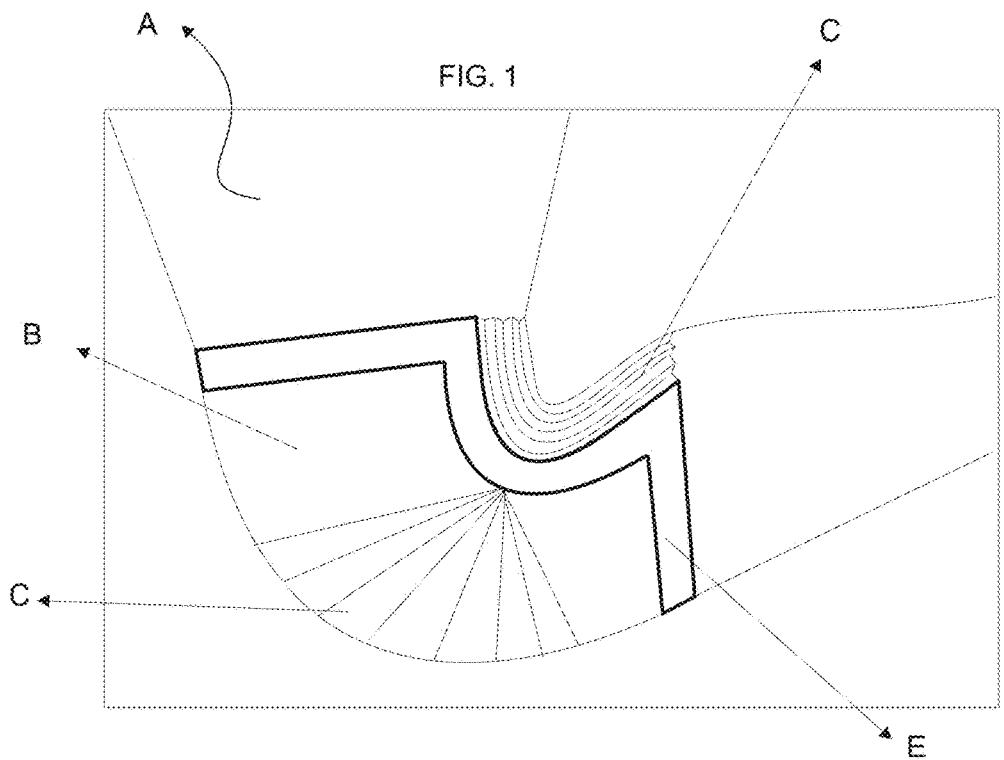
FIG. 1 illustrates the product added to the leg (A) of a person, more specifically to the knee and it is possible note that when bending the knee, the portions pleats/ruffles (C) of the objects open so that the movements can be performed as well as to suit the various body proportions. The therapeutic portion, form a pouch (B) on the objects, which contain a gel. The tracks (E) strengthen the attachment to the skin helping objects to stick to the body, even though the silicone itself is already highly adherent, avoiding slipping so that they do not come out of the place.
Figure 2:
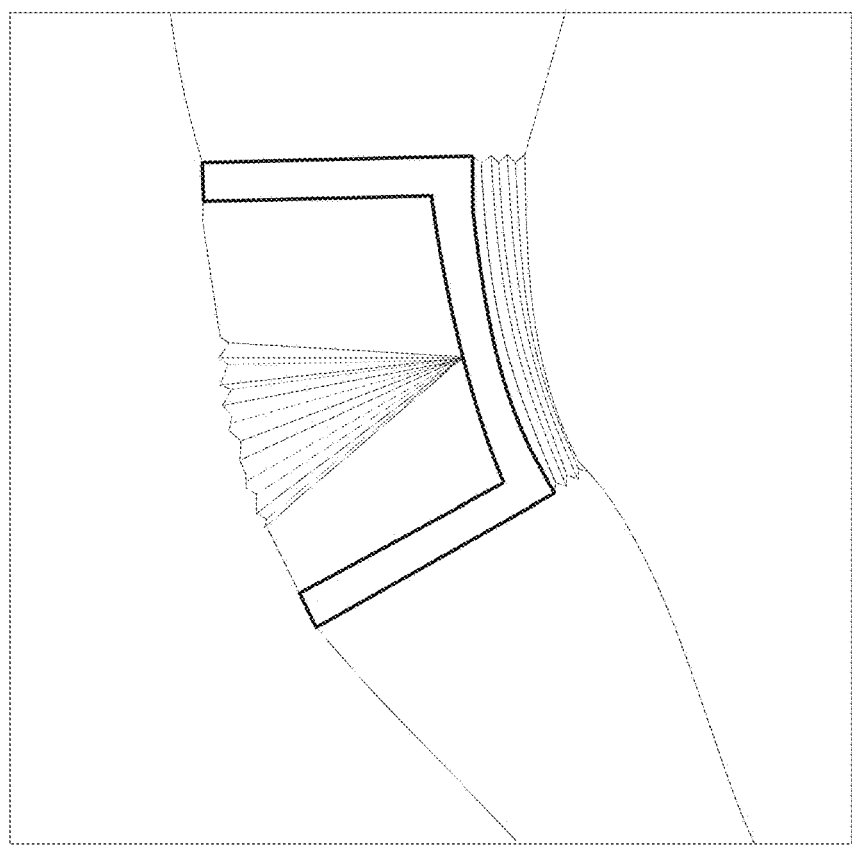
FIG. 2 shows the object again added to a knee where the person has not fully bent the leg.
Figure 3:
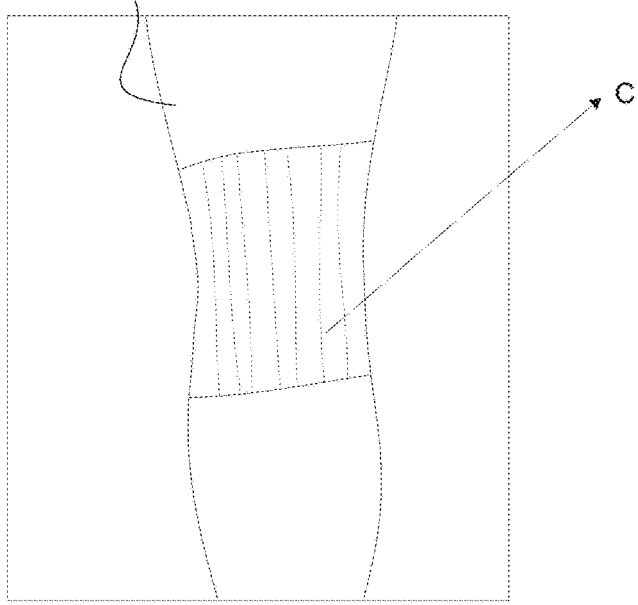
FIG. 3 reveals a rear view of the object in a leg where you can see another point ruffle/ruffle (C) fitted to the back of a leg (A).
Figure 4:
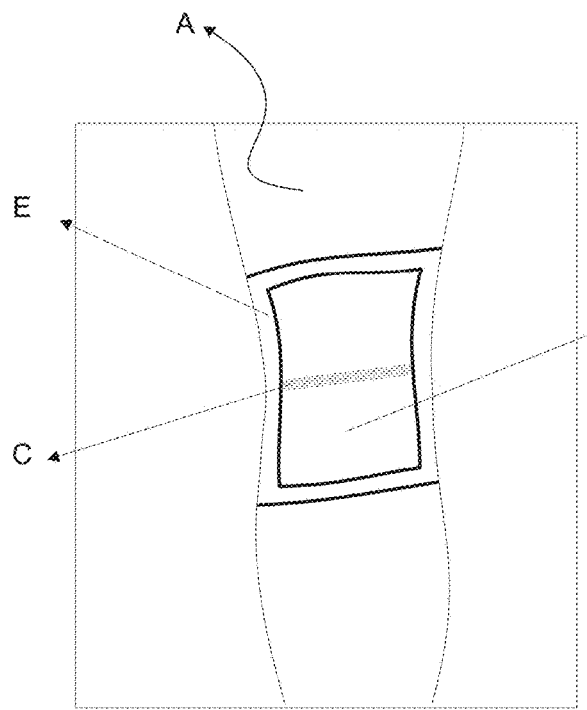
FIG. 4 reveals a front view of the object in a leg (A) where it is possible to observe the portion pleated/pleated (C) on one unbent (A) leg.
Figure 5:
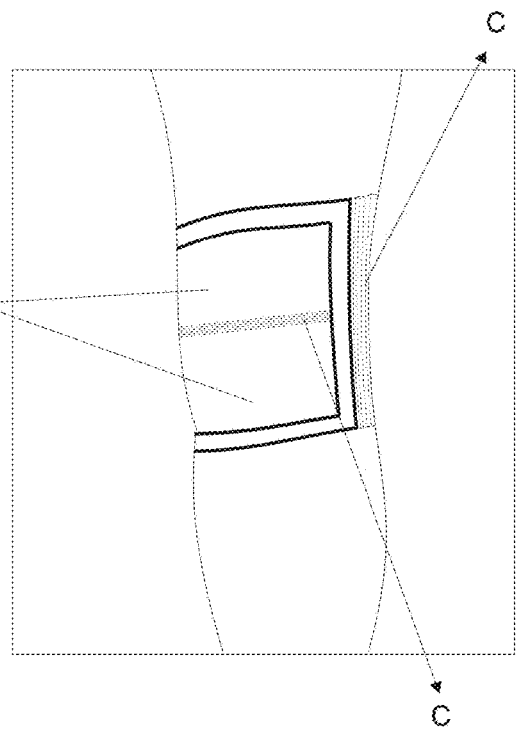
FIG. 5 reveals a side view of the object in a leg (A) where it is possible to observe the portion pleated/pleated (C) on one unbent (A) leg.
Figure 6:
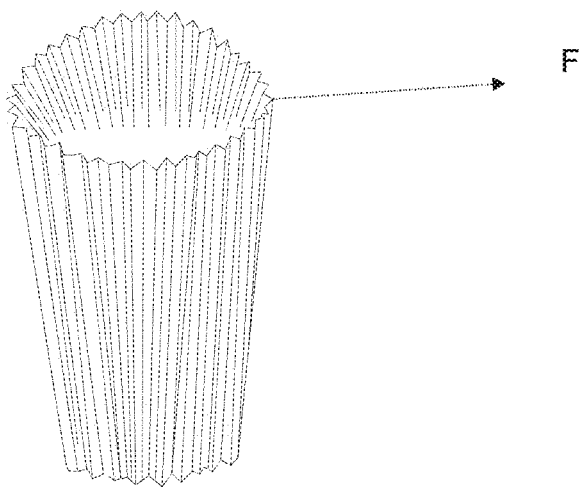
FIG. 6 refers to a new layout, in format of sleeve (sleeve) (F), having your body completely ruffle/ruffle (C), for use on shin, thigh, upper arm and forearm and with gel insert (B) for use as cooled or heated pads.
Figure 7:
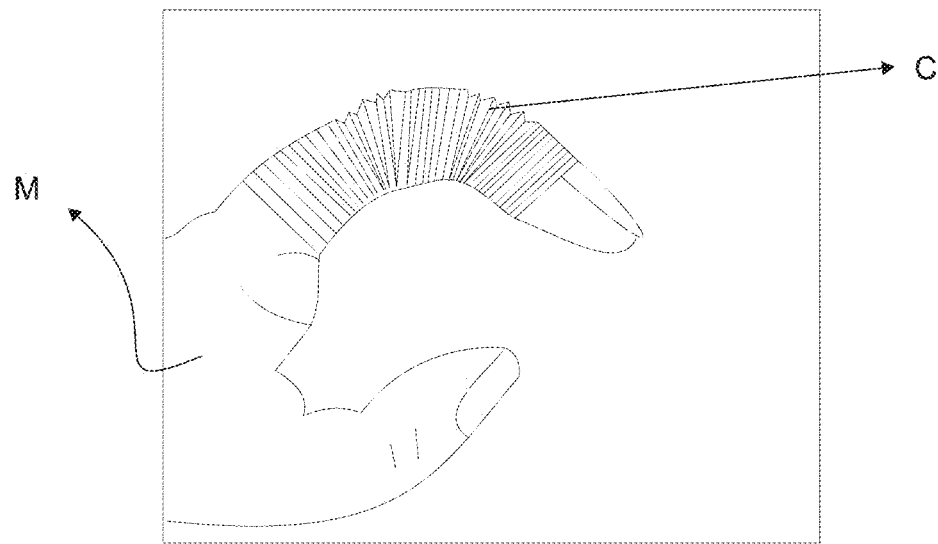
FIG. 7 shows a finger (M) where a sleeve (sleeve) (F) that has portions pleats/ruffles (C) to facilitate movement and to fit to size, as well as FIGS. 8 and 9 represent front and rear views, respectively, of the hose (F) with pleated/pleated body (C) horizontally (FIG. 8) and vertically (FIG. 9) and with gel insert (B) for use as cooled or heated compresses.
Figure 8:
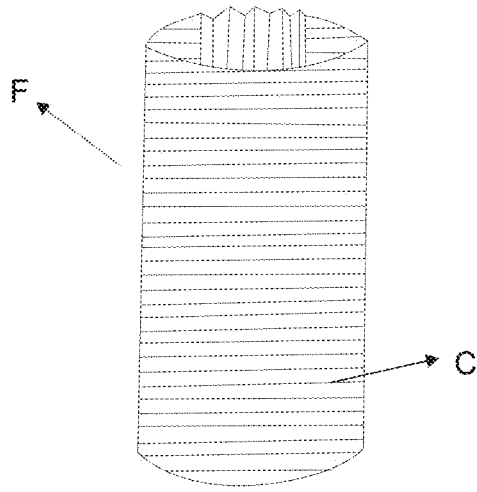
Figure 9:
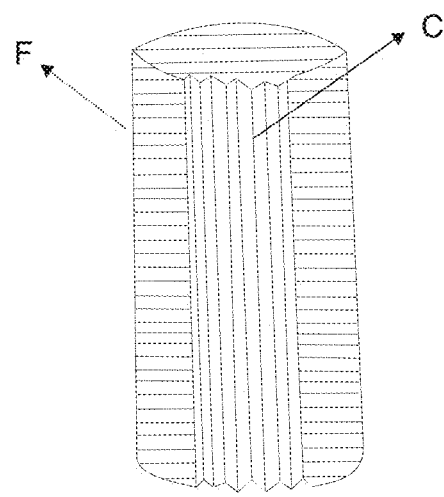
Figure 10:
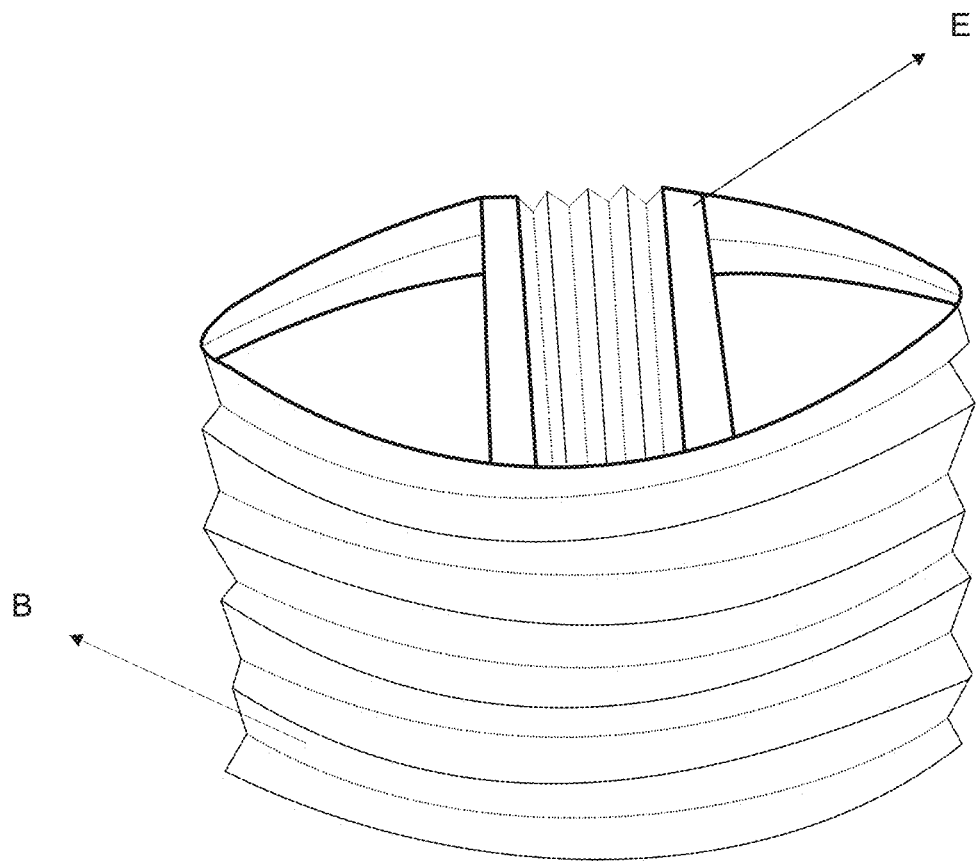
FIG. 10 shows a wristband for the wrist of the sleeve type (sleeve), with pleated material (C), reinforcement (E) and with gel insert (B) for use as cooled or heated pads.
Figure 11:
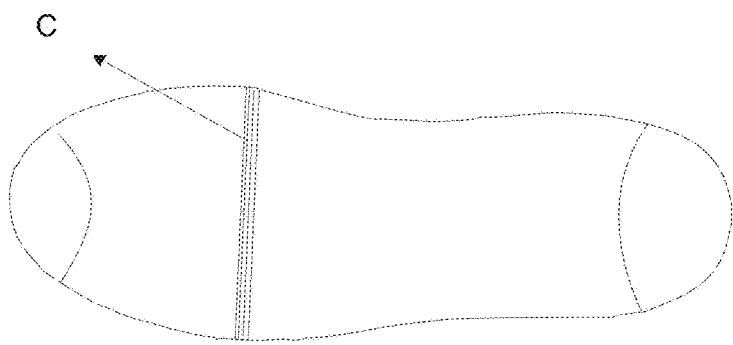
FIG. 11 shows the sole of a sock or a insole, where it is possible to verify that the ruffle/ruffle (C) can be presented in parts objects.
Figure 12:
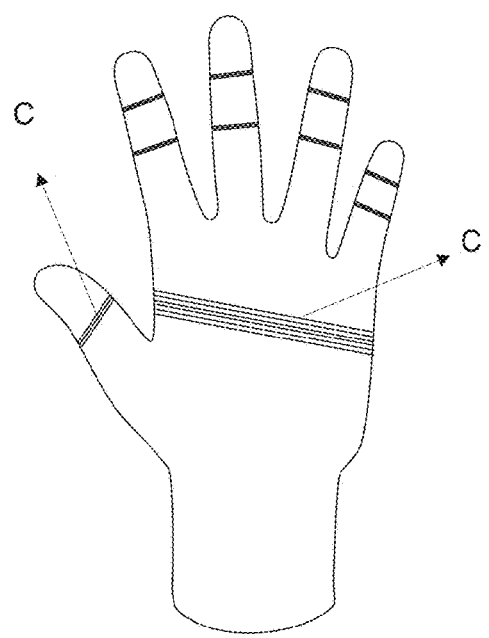
FIG. 12 illustrates a glove, in which the pleats/ruffles (C) present in the knuckles of the fingers and in the Palm.
Figure 13:
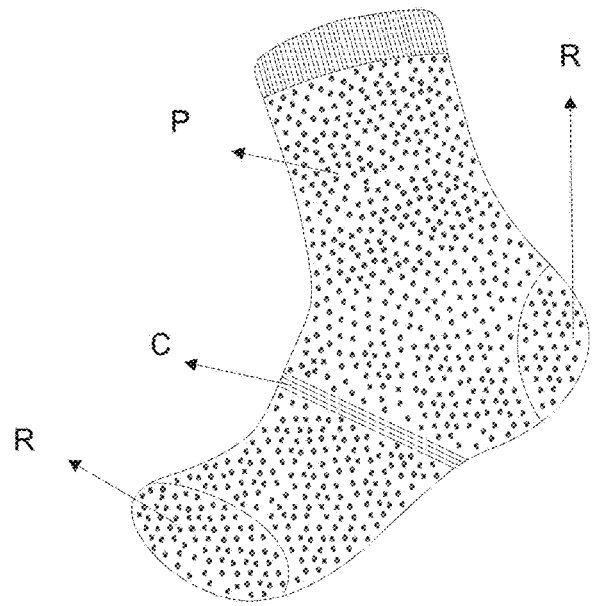
FIG. 13 represents a comfort sock with perforations (P) to facilitate skin breathing, sections reinforced (R) in the toes and heel, also having a pleated/pleated portion (C).
Figure 14:
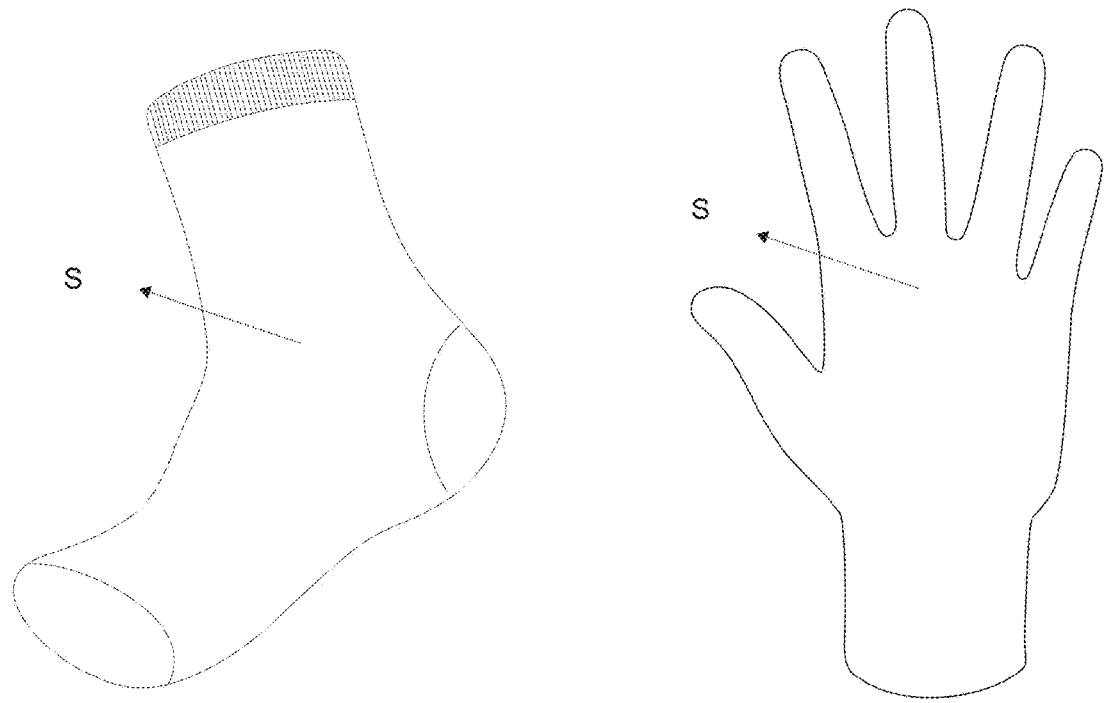
FIG. 14 reveals smooth silicone socks/gloves (S) that can be used with the insertion of cosmetic or medicated creams/gels/ointments. Sayings creams/gels/ointments have their active ingredients potentiated since the object will not be able to easily evaporation inside the silicone sock or glove.
Figure 15:
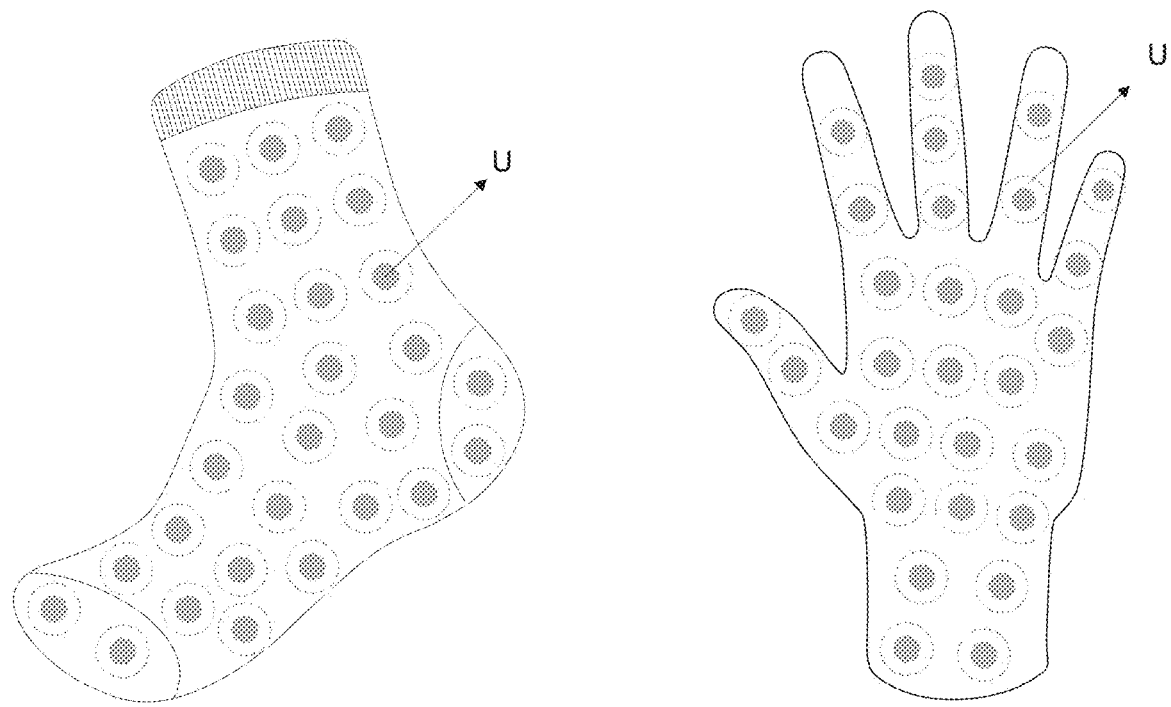
FIG. 15 reveals socks/gloves made of silicone with massaging points (U) that are used for massaging the body portion to which they are disposed.

For this purpose, the perforations (P) facilitate breathing of the skin so that there is no excessive moisture; the sections reinforced (R) complement the material for greater comfort at strategic points; the pleated/pleated area (C) receives a strip of pleated material adapting the objects to different sizes of users, as well as to allow movement when used on joints; the objects in smooth or pleated silicone with closed finish, type socks and gloves, can receive creams/gels/ointments for use moisturizing or therapeutic and as silicone does not absorb the products applied and being anti fungal, the treatment is more effective and safer; the massaging points (U) are used to massage the body portion in which are willing.

DETAILED DESCRIPTION OF THE OBJECT

In accordance with figures the objects obtained are comfortable, adaptable and made with Liquid Silicone Rubber (LSR). O silicone used is an FDA and Anvisa approved material, and it is safe to use objects that have direct contact with the human skin. Silicone is cured in molds, with or without the insertion of gel, it can be cooled or heated. These molds idealize objects that can be used for products related to various physical activities or exercises, for walking, resting, practicing sports, treatments/physical rehabilitation, skin care, etc., in the most diverse parts of the body, providing comfort, protection, care and rehabilitation of the skin and musculature.

Used in cases where there is direct contact, of any type of device, sporty or not, with the skin, producing friction, the objects prevent friction arising movements avoiding their harmful consequences. Your objects provide a barrier, creating a second skin, that prevents direct skin contact with the apparatus used (such as social and sports shoes, appliances exercises, etc.) avoiding blisters, corns, and others injuries caused by friction.

Another function of objects is to help in the healing of cuts, treatment of dryness or cracks in the skin and pain relief, muscle treatment, etc. For this the smooth silicone objects (S), with or without elements ruffles/ruffles (C). The skin can receive products medicinal, therapeutic or cosmetic, and the action moisturizing or healing will be more effective, as the silicone does not absorb products inserted into the skin preserving its properties.

Another application on objects is that of perforations (P) in socks, gloves, and other objects that allow breathing of the skin. Therefore, said perforations (P) allow ventilation that prevents moisture and accumulation of sweat and its consequences.

The pleated/ruffled portion (C) on the objects has two functions, one being for mobility, when the part pleated/folded opens so that the movement, of the joints, can be done without hindrance, another is when the pleated/folded portion opens for object to fit to the size of the users. Therefore, the portion pleated/folded is a novelty in these types of objects making them more comfortable and efficient. In the case of sleeve (sleeve) (F), for use on the fingers pleated/folded, to allow movement, incorporates the entire length of the object due to two joints being close to each other, and this sleeve (sleeve) it can also be adapted to other parts of the body.

Because they are made with Silicone Rubber Liquid (LSR), objects with reinforcement thickness (E) if adhere to the skin, adapting to the body part without leaving the place during use.

At strategic points of the object, where there is greater friction, sections are reinforced/thick (R) for greater protection and comfort of users.

Socks and gloves have cracks in the soles and palms with anti-slip function, allowing the user to walk without slipping and handling objects without them they slip from your hands.

The Liquid Silicone Rubber (LSR) used has good stability resisting high and low temperatures, it has superior compatibility with human tissue and fluid, is resistant to bacteria/microbes/fungi, odorless, tasteless and can be formulated to meet sanitary requirements, it can also be sterilized with a variety of methods, it is extremely resistant, has good durability (tensile strength and wear resistance) and has excellent flexibility.

The invention claimed is:

1. A liquid silicone rubber (LSR) product comprising:
a cured silicone body that includes a first end, a second end opposing the first end, a body length separating the first and second ends of the cured silicone body, a pleated portion disposed along the body length, a smooth portion flanking the pleated portion, a pouch formed on the body, disposed along the body length, and containing gel inside of walls forming the cured silicone body, strips disposed along the first and second ends of the body, forming a sleeve shape, defining perforations thereon that span through the body.

2. The LSR product according to claim 1, wherein the body includes at least one reinforced section disposed along the body length.

3. The LSR product according to claim 1, wherein the body includes an inner surface, an outer surface opposing the inner surface, and massaging points from on the inner surface of the body and disposed along the body length.

* * * * *